United States Patent
Dalmia et al.

(10) Patent No.: US 7,410,558 B2
(45) Date of Patent: Aug. 12, 2008

(54) METHOD AND APPARATUS FOR DETERMINING A TOTAL CONCENTRATION OF A COMPONENT IN A MIXTURE OF COMPONENTS

(75) Inventors: Avinash Dalmia, Hamden, CT (US); Otto J. Prohaska, Seymour, CT (US)

(73) Assignee: PerkinElmer LAS, Inc., Shelton, CT (US)

( * ) Notice: Subject to any disclaimer, the term of this patent is extended or adjusted under 35 U.S.C. 154(b) by 317 days.

(21) Appl. No.: 10/675,629

(22) Filed: Sep. 30, 2003

(65) Prior Publication Data

US 2005/0069456 A1     Mar. 31, 2005

(51) Int. Cl.
*G01N 27/26* (2006.01)
*G01N 1/18* (2006.01)
*G01N 1/22* (2006.01)
*G01N 30/02* (2006.01)
*G01N 1/00* (2006.01)

(52) U.S. Cl. ............... 204/424; 436/177; 436/181; 73/23.4; 73/61.58; 204/410

(58) Field of Classification Search ............ 422/71, 422/83–94; 436/177, 181; 73/23.4, 61.58; 204/410, 424
See application file for complete search history.

(56) References Cited

U.S. PATENT DOCUMENTS

| | | | | |
|---|---|---|---|---|
| 4,663,113 A | * | 5/1987 | Jester et al. | 376/256 |
| 4,668,635 A | * | 5/1987 | Forster | 436/134 |
| 4,820,386 A | * | 4/1989 | LaConti et al. | 205/779.5 |
| 5,612,225 A | * | 3/1997 | Baccanti et al. | 436/114 |
| 5,637,506 A | * | 6/1997 | Goken et al. | 436/57 |
| 6,592,817 B1 | * | 7/2003 | Tsai et al. | 422/62 |
| 6,830,730 B2 | * | 12/2004 | Rhodes | 422/78 |
| 7,013,707 B2 | * | 3/2006 | Prohaska et al. | 73/23.4 |
| 2003/0106811 A1 | * | 6/2003 | Prohaska et al. | 205/783.5 |

* cited by examiner

*Primary Examiner*—Jill Warden
*Assistant Examiner*—Keri A Moss
(74) *Attorney, Agent, or Firm*—St. Onge Steward Johnston & Reens LLC (57) ABSTRACT

The invention relates to a method and apparatus for determining a total concentration of a component in a sample, including a reactor for oxidizing or reducing the sample, a chromatographic column coupled to the reactor for separating the component in the sample, and an electrochemical gas sensor coupled to the chromatographic column for detecting the component. In further embodiments, a filter may be used instead of or in addition to the column. Moreover, multiple sensors may be used instead of or in addition to the column for simultaneously detecting multiple components.

5 Claims, 11 Drawing Sheets

METHOD AND APPARATUS FOR DETERMINING A TOTAL CONCENTRATION OF A COMPONENT IN A MIXTURE OF COMPONENTS

FIELD OF THE INVENTION

The invention relates to a method and apparatus for determining a total concentration of a gas or liquid component in a respective mixture of gas or liquid components.

BACKGROUND OF THE INVENTION

Detecting for the presence of particular components may be useful for a variety of reasons. With respect to environmental concerns, an apparatus for detecting pollution or industrial emission, whether in the liquid or gaseous state, may alert an individual responsible for limiting such contaminants as to when a given quantity of pollution has entered water systems or the atmosphere. A gas detection unit may be used for detecting the presence of dangerous chemical compounds, such as carbon monoxide, in a mixture of gases. In the medical field, a gas detection unit may be used for detecting a particular gas in equipment, such as an oxygen inhalation machine, for alerting staff as to the amount of oxygen remaining in the reservoir or given to the patient.

Known methods and apparatuses have been developed to detect the presence of gases or liquids. Typical systems include gas chromatography, ion chromatography, electrolytic conductivity detection, and conductometric measurement. However, these detection systems have generally been expensive, cumbersome, or shown to have low sensitivities and slower response times. In situations where a generally quick response time may be desired, such as detecting toxic gases or a lack of oxygen in an oxygen inhalation machine, detection systems having enhanced abilities to quickly detect particular gases or liquids are usually favorable.

Systems for detecting gases appear to be disclosed in U.S. Pat. No. 4,843,016 to Fine, U.S. Pat. No. 5,268,302 to Rounbehler et al., U.S. Pat. No. 6,458,328 to Wreyford, and U.S. Pat. No. 5,152,963 to Wreyford. In these systems, a gas chromatograph column appears to be placed prior to the reactor so that components of the mixture may be separated from one another prior to being oxidized and/or reduced. This apparatus often permits particular compounds to be detected upon exiting the reactor. For example, a detector coupled to the reactor may be used to detect $H_2S$ while other compounds, such as $H_2O$, $CH_4$, $SO_2$, or $SO_3$, may not be detected by the detector.

However, if a total concentration of hydrogen is desired using the apparatuses shown in Fine, Rounbehler, or two Wreyford patents, multiple detectors may be needed to detect all of the compounds containing hydrogen, such as a detector for detecting $H_2O$ and another detector for $CH_4$. The detectors' results may thereafter need to be summed, which may also introduce measurement error with respect to each detector, so that the total amount of hydrogen may be determined.

U.S. Pat. No. 4,293,308 to Sisti et al. ("Sisti") appears to relate to a method and apparatus for determining a total concentration of sulfur in a gas sample. Sisti seems to teach a reactor for combusting a gas sample and oxygen, followed by a gas chromatograph column for separating components of the combustion mixture from one another. The separated components seem to then be conveyed to a known thermal conductivity detector ("TCD") for detection.

Figure 1:
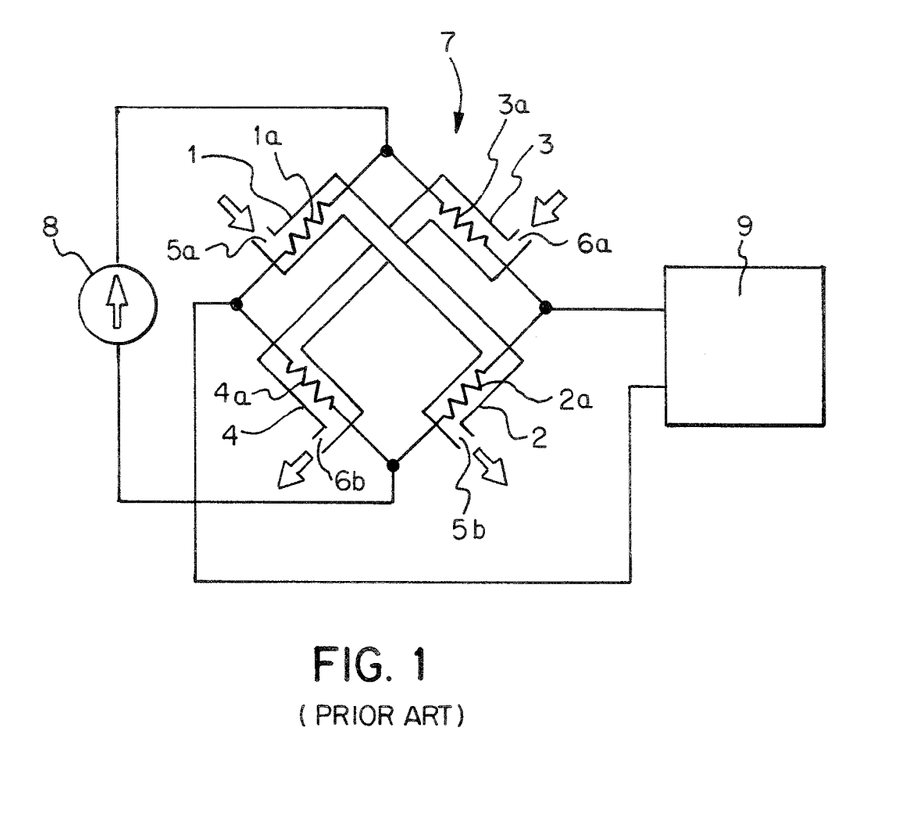
FIG. 1 depicts a thermal conductivity detector known in the prior art.

FIG. 1 depicts a conventional TCD in accordance with the prior art. As shown, first, second, third, and fourth cells 1,2, 3,4, respectively, appear to contain first, second, third and fourth heaters $1a$, $2a$, $3a$, and $4a$, respectively. Fluid being examined is typically led from an inlet $5a$ (see arrow) of the first cell 1, made to flow through first cell 1 and second cell 2, and led out of an outlet $5b$ (see arrow) of second cell 2. A reference fluid is usually led from an inlet $6a$ (see arrow) of third cell 3, made to flow through third cell 3 and fourth cell 4, and led out of an outlet $6b$ (see arrow) of fourth cell 4. In addition, first, second, third and fourth heaters $1a$, $2a$, $3a$ and $4a$, are most often connected to form an electrical bridge 7 and a predetermined current is normally supplied from a constant current supply 8 to bridge 7.

When an unbalance voltage is generated in bridge 7, a detection circuit 9 may detect such unbalance voltage, and in that way, variation in thermal conductivity of the fluids being examined may be measured, wherein the variation may indicate the amount of a component present in a mixture.

However, TCDs may have limited detection capabilities. As described in U.S. Pat. No. 5,295,389 to Nagata ("Nagata"), TCDs seem to be adversely affected due to the flow of gases that are to be detected, resulting in inaccurate gas measurements.

Hence, the Sisti method and apparatus for detecting total sulfur concentration, due to the possible limitations of the detector, may have limited sensitivity and/or accuracy. Moreover, Sisti appears to relate to a method and apparatus that is limited to a determination of a single component and where a determination of multiple components may require multiple operations in succession.

What is desired, therefore, is an improved detection system that determines a total concentration of a component from a mixture of components. What is also desired is a detection system having enhanced sensitivity and accuracy. A further desire is a detection system that efficiently and contemporaneously detects total concentrations of multiple components. A still further desire is a detection system that efficiently detects total concentrations of multiple components while reducing interference from undesired components.

SUMMARY OF THE INVENTION

Accordingly, it is an object of the invention to provide a method and apparatus that determines a total concentration of a specified component in a mixture of components.

Another object of the invention is to provide a method and apparatus that determines the total concentration and having improved sensitivity and accuracy.

A further object of the invention is to provide a method and apparatus that efficiently and contemporaneously detects total concentrations of multiple components.

Yet another object is to provide a detection system that achieves the above objects while reducing interference from undesired components.

These and other objects of the invention are achieved by provision of a an apparatus for determining a total concentration of a component in a sample, including a reactor for oxidizing or reducing the sample, a chromatographic column coupled to the reactor for separating the component in the sample, and an electrochemical gas sensor coupled to the chromatographic column for detecting the component.

In further embodiments, the electrochemical gas sensor may also include a substrate having a surface for depositing electrodes thereon, an ionomer membrane in contact with the surface of the substrate and having a first surface and a second surface, an electrode in contact with the surface of the substrate, an opening extending from the first surface to the second surface in a location proximate to the electrode for defining a passage, and a gas in the opening and simultaneously contacting the electrode and the ionomer membrane for providing a three way contact between the gas, electrode, and ionomer membrane within the opening.

In another embodiment of the invention, an apparatus for determining a total concentration of a desired component in a sample is provided, including a reactor for oxidizing or reducing the sample, a filter coupled to the reactor for filtering out undesirable components and for permitting the desired component to pass through, and a detector coupled to the filter for detecting the component.

In a variation of this embodiment, the detector may be replaced with an electrochemical gas sensor or plurality of electrochemical gas sensors.

In another embodiment of the invention, an apparatus for determining a total concentration of various components in a sample is provided, including a reactor for oxidizing or reducing the sample, a first electrochemical gas sensor coupled to the reactor and having an adjustment mechanism and wherein the adjustment mechanism is selectively adjustable to detect for the presence of a selected one of a plurality of components. A second electrochemical gas sensor is also coupled to the reactor and has an adjustment mechanism, wherein the adjustment mechanism is selectively adjustable to detect for the presence of a selected one of a plurality of components. In this embodiment, the sensors may simultaneously detect for the presence of two gas components in the sample. Additional sensors may permit simultaneous detection of multiple components In further embodiments, the apparatus may also include a filter coupled to the reactor for filtering out undesirable components and for permitting desirable components to pass through to the first and second electrochemical gas sensors.

In another aspect, a method for determining a total concentration of a component in a sample is provided, including the steps of oxidizing or reducing the sample in a reactor, separating the component from the sample using a separation device, and coupling an electrochemical gas sensor to the separation device for detecting the component.

The method may also include the step of separating the component from the sample using a gas chromatograph column.

The electrochemical gas sensor may be provided in accordance with the steps of providing a substrate having a surface for depositing electrodes thereon, depositing an electrode on the surface, contacting an ionomer membrane with the electrode, providing an opening in the ionomer membrane in an approximate area of the electrode, extending the opening from a first surface of the ionomer membrane to a second surface of the ionomer membrane for defining a passage, and placing a gas in the opening and simultaneously contacting the gas with both the electrode and ionomer membrane within the opening.

In a further aspect, the method may include coupling a plurality of electrochemical gas sensors to the separation device for detecting multiple components. In yet a further aspect, the method may include filtering out undesirable components and permitting desirable components to pass through.

In another aspect of the invention, a method for determining a total concentration of a component in a sample is provided, including the steps of oxidizing or reducing the sample in a reactor, filtering out undesirable components and permitting a desirable component to pass through using a filter, and coupling a detector to the filter for detecting the desirable component. The detector may further be replaced with an electrochemical gas sensor to the filter for detecting the desirable component.

The invention and its particular features and advantages will become more apparent from the following detailed description considered with reference to the accompanying drawings.

DETAILED DESCRIPTION OF THE DRAWINGS

Figure 2:
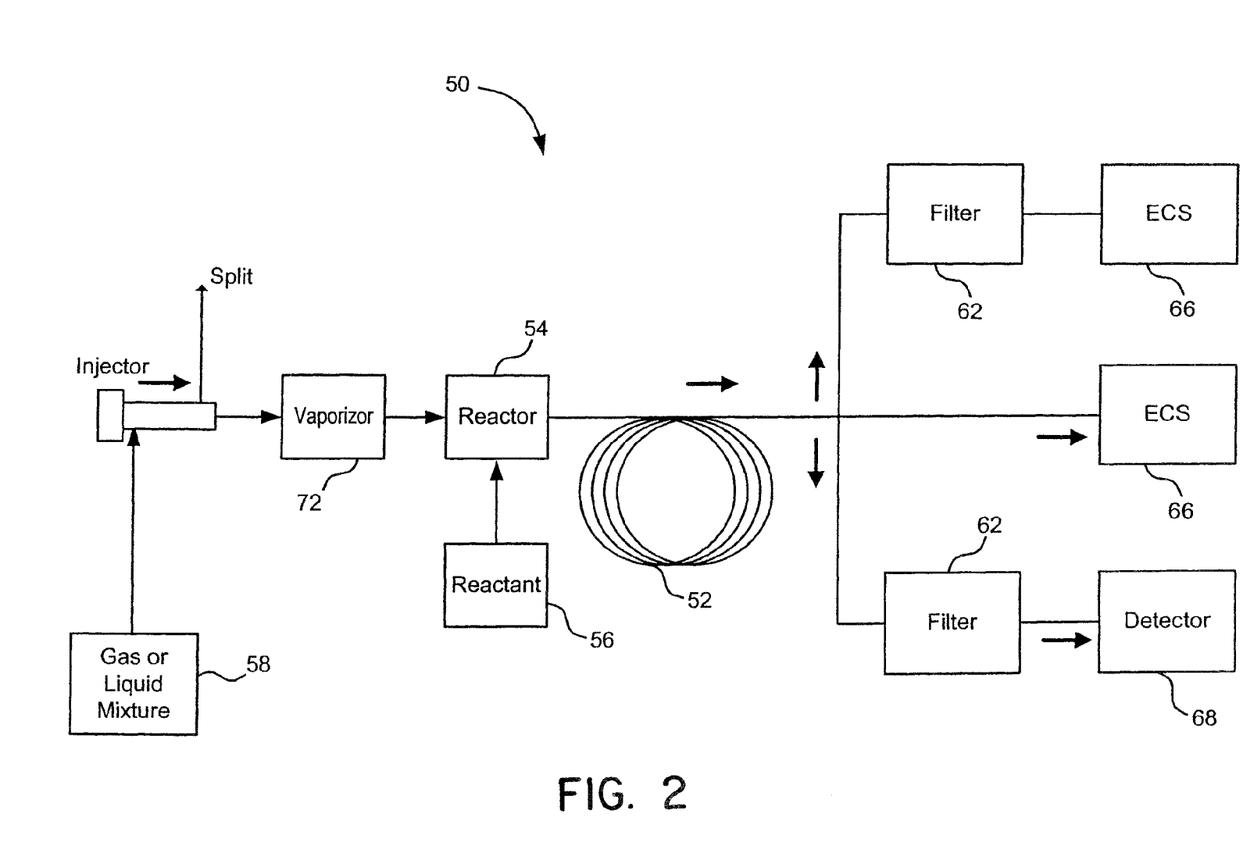
FIG. 2 depicts an apparatus for determining a total. concentration of a gas component in a gas mixture in accordance with the invention.

In accordance with the invention, FIG. 2 depicts the apparatus 50 for determining a total concentration of a component, whether in a gaseous or liquid state, in a mixture, or sample, of gases or liquids. Apparatus 50 further includes reactor 54 for oxidizing and/or reducing the mixture so that the desired component may be detected by sensor 66. Typically, a component desired to be detected by sensor 66, but which is not easily detectable, would be oxidized/reduced by reactor 54. As shown in FIG. 2, reactor 54 oxidizes/reduces a desirable component by heating the component together with a reactant gas 56 at a specified temperature.

Although apparatus 50 may be used with either a gas or liquid state mixture 58, if mixture 58 is in the liquid state, the volume of mixture 58 should be low enough such that, upon being heated inside reactor 54, mixture 58 converts into a gaseous state so that component, now in the gaseous state, may be detected by sensor 66. It is desired for the entire mixture 58 to convert to a gaseous state because any component remaining dissolved in a liquid state mixture may not be easily detected by sensor 66. Hence, in the event a volume of liquid state mixture 58 may not convert entirely to a gaseous state inside reactor 54, vaporizer 72 is placed between the injector and reactor 54 because reactant 56, if utilized to optionally facilitate oxidation and/or reduction, is a gas and may be mixed with mixture 58. In further embodiments, vaporizer 72 may be placed in any location where mixture 58, in the liquid state, is to be converted to a gaseous state, such as between reactor 54 and gas chromatograph column ("GC") 52 or between GC 52 and sensor 66.

In some embodiments where the desired components are easily detected, such as $H_2S$ in a gaseous state, reactor 54 and/or vaporizer 72 may be omitted from apparatus 50, which results in mixture 58 exiting the injector and directly entering GC 52. In other embodiments, if mixture 58 is a liquid, reactor 54 and/or vaporizer 72 would be needed to heat mixture 58 until mixture 58 converts into a gaseous state prior to entering GC 52.

GC 52 acts as a separation device and is used to separate the mixture or sample 58 into its respective components. Upon exiting GC 52, the desirable component is ultimately detected by an electrochemical gas sensor 66, which is coupled to an end of GC 52 where the gas components are exiting GC 52. The combination of sensor 66 being coupled to GC 52 provides a system 50 for detecting a component having enhanced sensitivity and response time because sensor 66 provides numerous advantages over conventional detector cells 10, as shown and described under FIG. 1.

Sensor 66 reduces the need for a component of the sample to be absorbed and dispersed in an electrolyte solution in order for an electrical measurement to be taken across electrodes in contact with the solution. Sensor 66 detects gas as the gas comes in contact with an electrode, thereby reducing response time and increasing sensitivity. Moreover, the resolution, or detection capability, of sensor 66 is typically in the range of parts per billion, which is generally more sensitive than the conventional detector cell shown in FIG. 1. Sensor 66 and its limitations are more particularly described under FIGS. 7-10.

Figure 3:
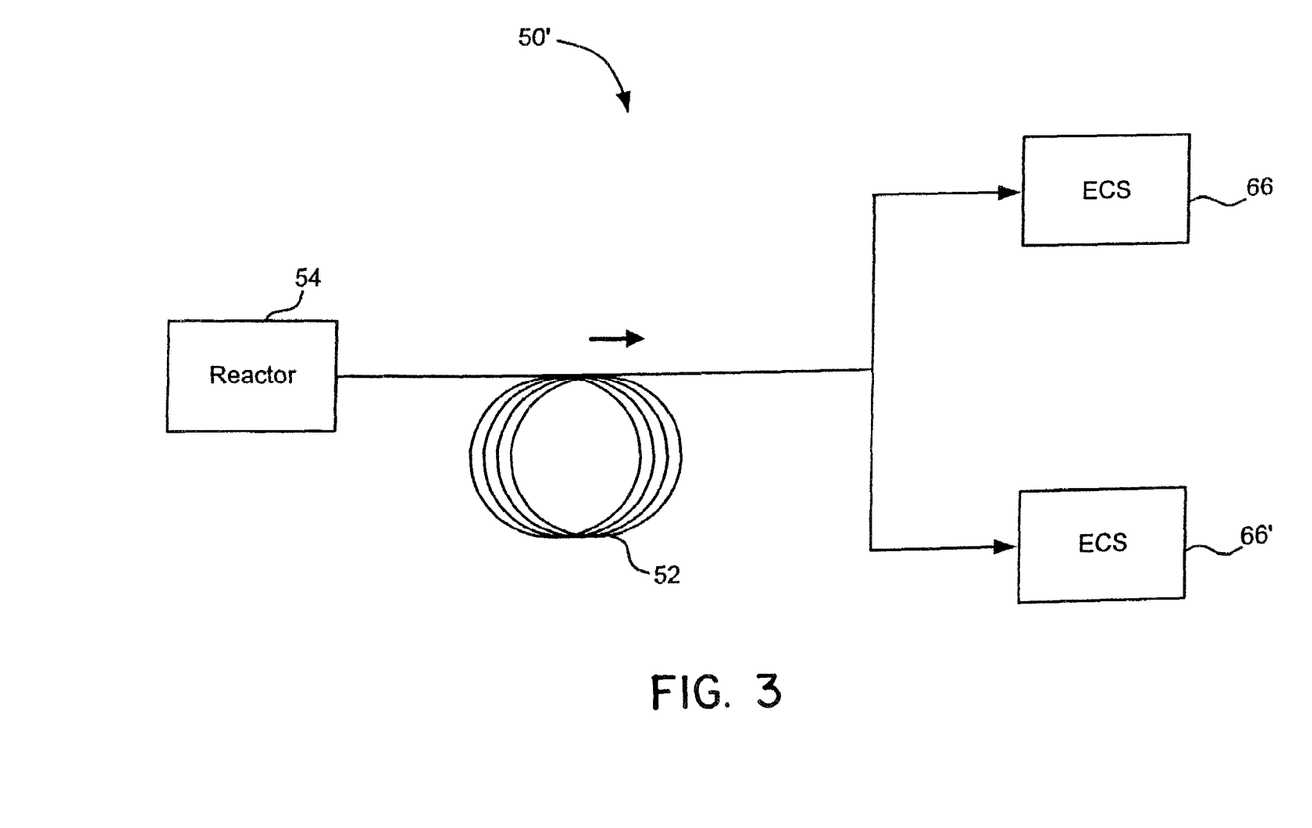
FIG. 3 depicts one embodiment of the apparatus shown in FIG. 2.

One embodiment of apparatus 50 is to have sensor 66 directly coupled to GC 52. In further embodiments, a plurality of sensors may be directly coupled to GC 52. As shown in FIG. 3, sensors 66 and 66' are connected in parallel to GC 52. It is understood that apparatus 50' of FIG. 3 should not be limited to two sensors but may have any number of sensors and that two sensors are shown for exemplary purposes.

Sensor 66' has the same limitations as sensor 66 and, to reduce repetition, only sensor 66 will be described.

In the embodiment shown in FIG. 3, apparatus 50' is capable of simultaneously detecting two desired components due to having both sensors 66 and 66'. More components may be simultaneously detected by adding more sensors. Sensors 66 and 66' are preset to detect for the presence of different components by varying the applied potential across the sensing electrode (enumerated as 103 and 138 of FIGS. 7 and 8) of each sensor so that gases having an electrical signal that match the preset potential of the respective sensor are detected.

Figure 4:
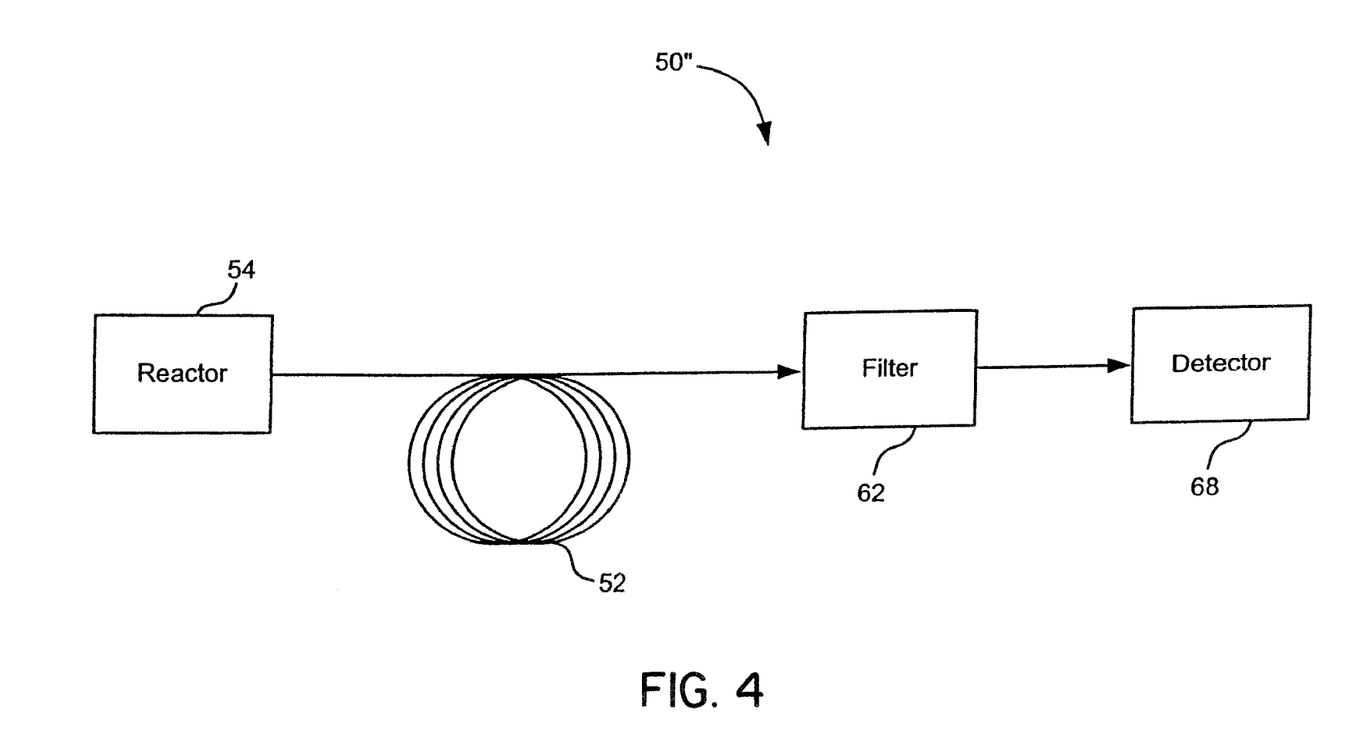
FIG. 4 depicts another embodiment of the apparatus shown in FIG. 2.

FIG. 4 depicts another embodiment of the invention where, instead of coupling sensor 66 to GC 52, filter 62 is coupled to GC 52 for removing undesirable components from mixture 58. As described above, GC 52 merely separates components from one another where all components going into GC 52 exit GC 52 but exit in a particular order. Desirable and undesirable components exit GC 52 and, in some cases, undesirable components may interfere with the detection of desirable components. Therefore, filter 62 is used to enhance, or facilitate, detection of the desirable components by removing undesirable components. Filter 62 prevents particular components from passing through based on the chemical properties of the components.

Hence, filter 62 may filter out all water or other compounds from passing through to detector 68. Examples of filter 62 that removes undesirable components include any membrane dryer or drying agents, such as Nafion or magnesium perchlorate. Filter 62 suppresses undesirable components by reducing its ability to interfere with the detection of desirable components. In a further example, $H_2S$ is difficult to detect with water present because water typically absorbs $H_2S$. In other words, $H_2S$ dissolves in water and, therefore, water is typically an undesirable component of the mixture having $H_2S$. With $H_2S$ being dissolved in or absorbed by water, proper detection of $H_2S$ is adversely affected and, hence, water lessens the likelihood of $H_2S$ being accurately detected by either detector 68 or sensor 66.

Figure 5:
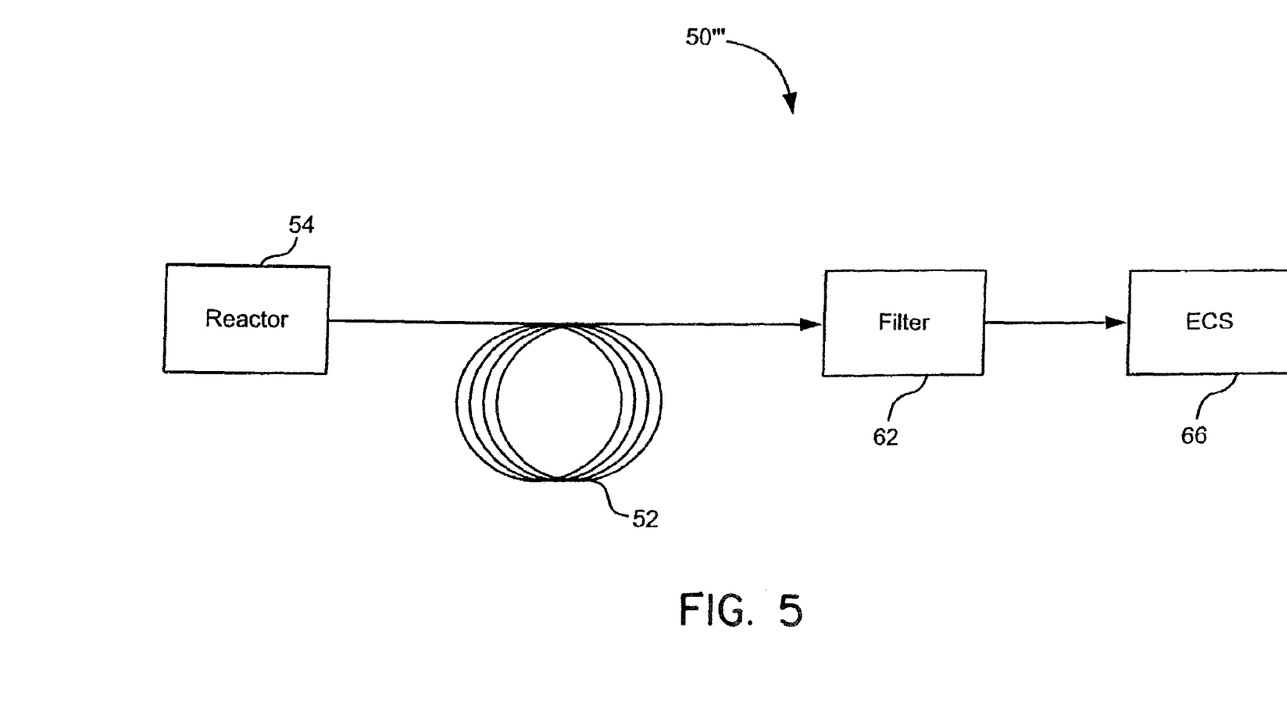
FIG. 5 depicts another embodiment of the apparatus shown in FIG. 2.

FIG. 5 depicts another embodiment of the invention where, instead of detector 68 shown in FIG. 3, sensor 66 is used to enhance detection capabilities to ppb over the limited detection capabilities of detector 68.

It should be known that in further embodiments, GC 52 may be omitted when separation of the components of the gas mixture are not needed to detect the desirable component, particularly where it is likely the desired components are not dispersed throughout the gas mixture. For example, if detection of $H_2S$ is desired and the remaining components of the gas mixture do not have any hydrogen or sulfur, GC 52 may not be needed because there would not be any hydrogen or sulfur to separate.

Figure 6:
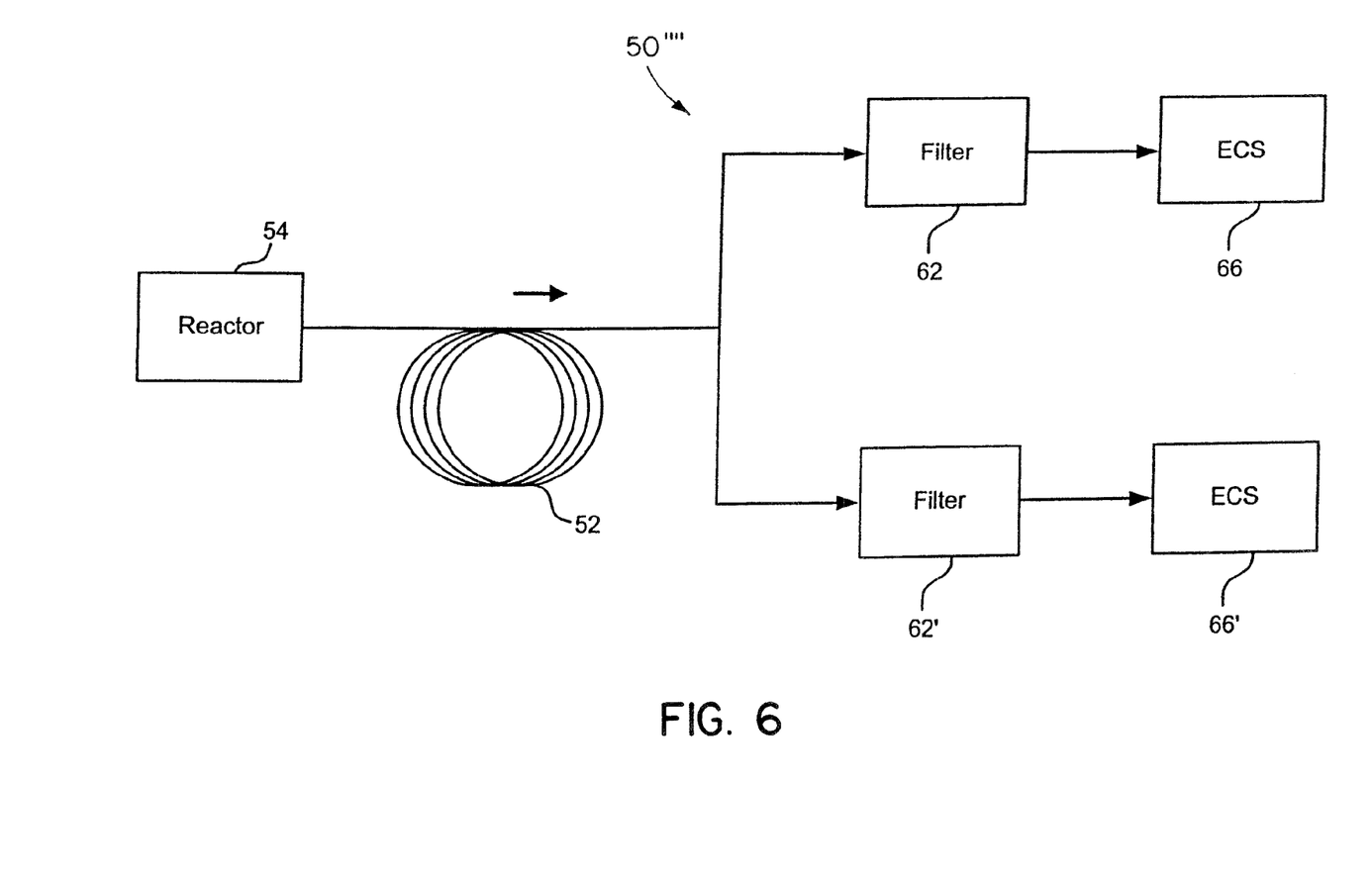
FIG. 6 depicts another embodiment of the apparatus shown in FIG. 2.

FIG. 6 depicts a further embodiment of the invention shown in FIG. 5, where multiple filters 62, 62' and sensors 66, 66' are employed to simultaneously detect several desirable components. Because filter 62' includes all of the limitations of filter 62, and to reduce repetition, filter 62 will be described hereinafter. As shown, sensors 66 and 66' are employed to, as described above, simultaneously detect at least 2 desirable components by presetting sensors 66 and 66' to different applied potentials across the sensing electrode of each sensor.

Filters 62 and 62' are used to enhance detection by removing or suppressing different types of undesirable components based on various chemical properties of the undesirable components. Filters 62 and 62' may be preset to chemically filter out predetermined undesirable components that are most likely to interfere with the component to be detected by the respective sensor 66 and 66'.

Figure 7:
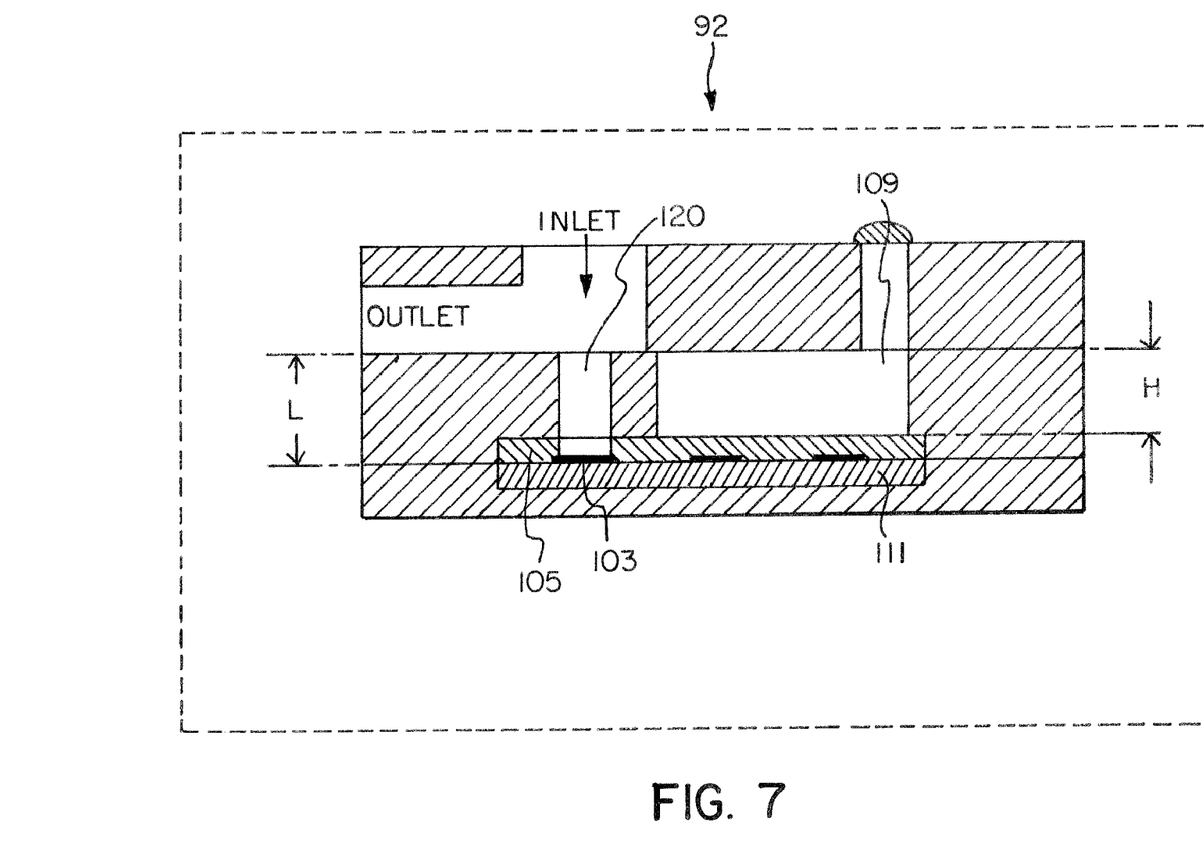
FIG. 7 depicts a sensor for use with the apparatus shown in FIG. 2.

FIG. 7 shows an electrochemical gas sensor of copending U.S. patent application Ser. No. 09/443,875, which may, but not necessarily, be used as sensor 66. As shown, electrochemical gas sensor 92 includes substrate 111, electrode 103, and ionomer membrane 105. Gas enters and exits sensor 92 through the inlet and outlet as shown. A portion of the gas entering sensor 92 diffuses through diffusion hole 120 and contacts electrode 103, which detects the type of gas present in sensor 66. As stated above, for the purposes of simplicity, sensor 66' will not be described but is understood to include the limitations of sensor 66.

To enhance sensitivity to sensor 92, a reservoir 109 is provided containing electrolyte solution to wet ionomer membrane 105. As shown, reservoir 109 and, therefore, the electrolyte solution is in contact with ionomer membrane 105. Because reservoir 109 is located on a same side of ionomer membrane 105 as diffusion hole 120, a length of diffusion hole is typically at least as long as a height of reservoir 109.

Figure 8:
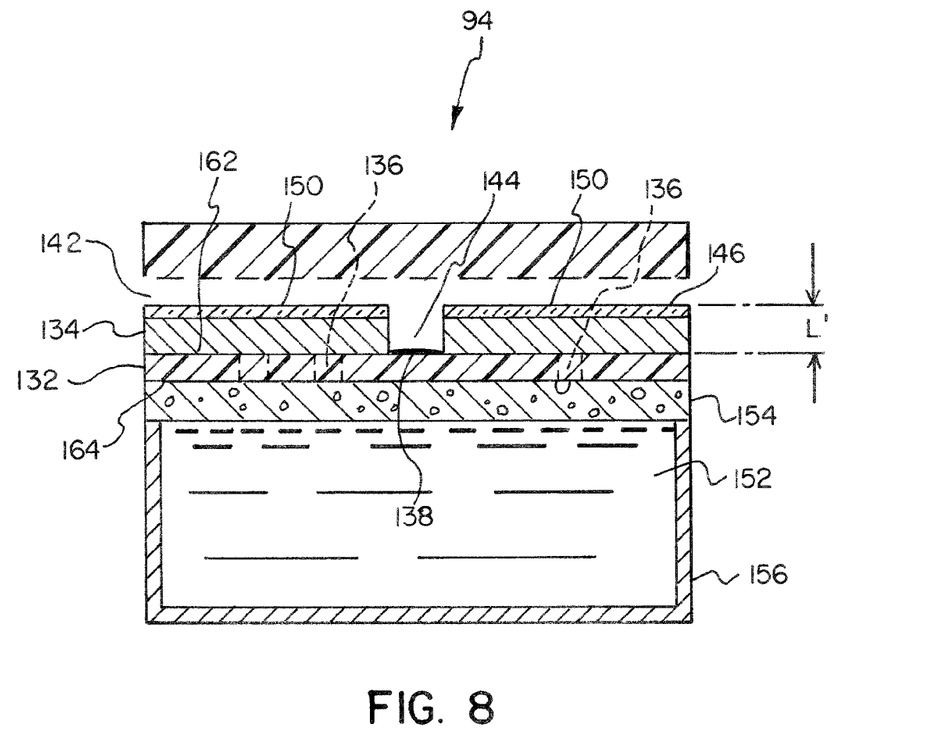
FIG. 8 depicts another sensor for use with the apparatus shown in FIG. 2.

FIG. 8 depicts another electrochemical gas sensor 94, which may, but not necessarily, be used as sensor 66. Sensor 94 includes substrate 132, ionomer membrane 134, and electrode 138. Gas enters sensor 94 through inlet 142 and is detected after diffusing through diffusion hole 144 to contact electrode 138, which is in contact with ionomer membrane 134. Gas exits sensor 94 through outlet 146. It is understood that the gas may flow in a reversed direction where outlet 146 is the inlet and inlet 142 is the outlet.

To enhance the sensitivity of sensor 94, ionomer membrane 134 is wetted by solution 152, which is contained in reservoir 156. In FIG. 7, electrolyte solution and reservoir 109 were placed on the same side of substrate 111 as electrode 103. Although the electrolyte solution wetted ionomer membrane 105 to enhance the sensitivity of sensor 92 in the same manner as solution 152 enhances the sensitivity of sensor 94, reservoir 109 being on the same side of substrate 111 inhibits a length L of diffusion hole 120 from being reduced, which would reduce gas diffusion time and thereby improve sensor sensitivity. As shown in FIG. 7, length L could not be shortened more than height H of reservoir 109. Therefore, time required for gas to diffuse from the inlet through diffusion hole 120 to contact electrode 103 was difficult to reduce due to the length L of diffusion hole being of a minimum dimension not less than the height H of reservoir 109.

Sensor 94 of FIG. 8 overcomes this disadvantage by wetting ionomer membrane 134, via hole 136 in substrate 132, with solution 152 located on a side of substrate 132 opposite from electrode 138. Because of the position of reservoir 156, length L' can be shortened, thereby reducing gas diffusion time and improving the sensitivity of sensor 94. The more length L' is reduced, the faster the response time of sensor 94. In some embodiments, length L' is less than 1.4 mm. In other embodiments, length L' is less than 1 mm. In further, embodiments, length L' is less than 0.5 mm. In still further embodiments, length L' is less than 0.1 mm. In fact, length L' or a thickness of ionomer membrane 134 may be reduced until it is flush with or below a surface of electrode 138. In some embodiments, diffusion hole 144 is eliminated because length L' is flush with or below a surface of electrode 138. All that is required is for ionomer membrane 134, of any length L', to be in contact with electrode 138 so that gas entering through inlet 142 provide a desired gas/ionomer membrane/electrode interface.

As a result of the reduced length L' of sensor 94, the response time of sensor 94 is less than approximately 2 seconds, more preferably less than approximately 1 second, and most preferably less than approximately 0.5 seconds. In some embodiments, the response time is less than approximately 0.1 seconds.

To further enhance sensitivity, a thickness of substrate 132 is reduced to improve wetting by solution 152. Substrate 132 is of an electrically non-conductive material for providing a surface upon which electrode 138 is placed. Optionally, substrate 132 is a thin foil having insulative, or electrically non-conductive, properties, such as Kapton or any other material. The foil may not metallic or conductive. The foil may also be flexible as compared to ceramic or glass. The thickness of the foil, or substrate 132, is generally less than approximately 4 mils and preferably less than approximately 1 mil. The thinner substrate 132, the faster ionomer membrane 134 is wetted and this positively affects sensor response time. Therefore, as the thickness of substrate 132 approaches 0 mils, the response time is further reduced.

Optionally, in some embodiments, sensor 94 may include wicking material 154 to facilitate or enhance wetting of ionomer membrane 134 by solution 152. Wicking material 154 is typically of a material that absorbs liquid, such as a sponge. Hence, as shown in FIG. 8, wicking material 154 will draw solution. 152 upwardly from reservoir 156 toward ionomer membrane 134.

As shown, reservoir 156 and substrate 132 are separable from one another where wicking material 154 is placed between reservoir 156 and substrate 132. In other embodiments, wicking material is placed within reservoir 156 and reservoir comes in contact with substrate 132. In further embodiments, substrate 132 and reservoir 156 are made not separable from one another but are formed as one unit. Wicking material 154 may optionally be used with any of these embodiments of reservoir 156 and substrate 132.

As shown in FIG. 8, substrate 132 further includes at least one hole 136 extending from a first surface 162 of substrate 132 to a second surface 164 of substrate 132, thereby forming a thru-hole, for permitting solution 152 to pass, or diffuse, through at least one hole 136 to contact ionomer membrane 134. In the embodiments where substrate 132 is a foil, or a thin non-conductive material, wicking material 154 would be positioned in a closer relationship to ionomer membrane 134 than where substrate 132 is of a thick material. Where substrate 132 is a foil, solution 152 absorbed by wicking material 154 would more easily wet ionomer membrane 134. Optionally, wicking material 154 would be in contact, through at least one hole 136, with ionomer membrane 134. In some embodiments, wicking material 54, in addition to or instead of being between substrate 132 and solution 152, is placed within at least one hole 136.

To further facilitate wetting of ionomer membrane 134 by solution 152, or optional wicking material 154, a plurality of holes 136 are placed in substrate 132. It is understood that hole 136 is of any diameter, length, shape, or dimension. Also, the more holes 136 in substrate 132, in any location, the better ionomer membrane 134 is wetted. Hence, the hole 136 or plurality of holes 136 may act as a form of wetting control to ionomer membrane 134, as too much wetting or too little wetting negatively affects sensitivity. Moreover, hole 136 may be, in addition or instead of being round, a square shaped or polygonal shaped hole. Hole 136 may further be a slit or aperture of any kind. All that is required of hole 136 is that it provides a passage from first surface 162 to second surface 164 so that solution 152 diffuses through hole 136 to contact ionomer membrane 134.

Figure 9:
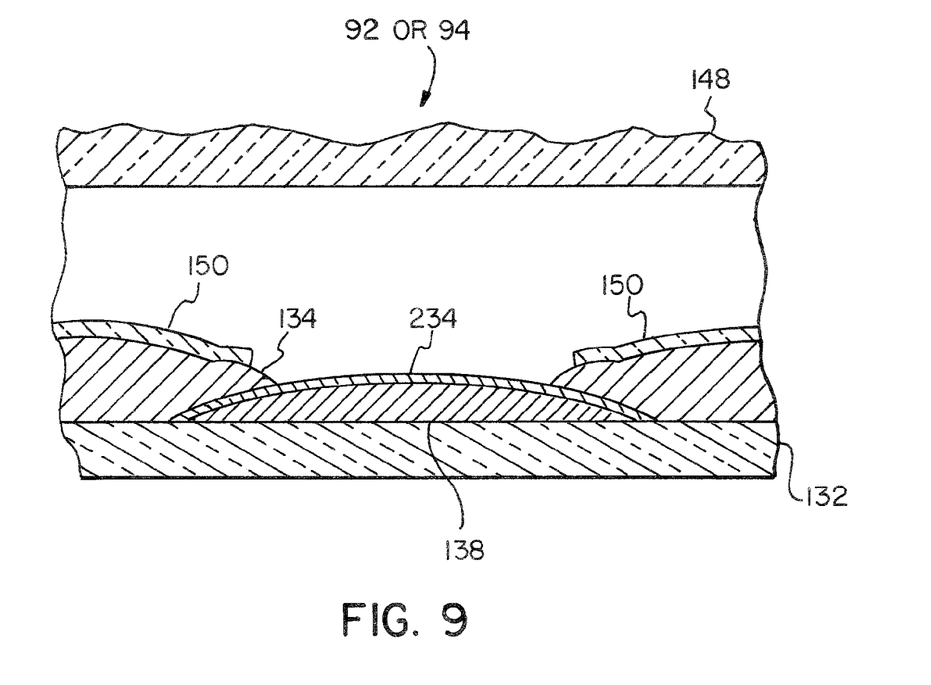
FIG. 9 more particularly depicts an electrode to be used with the sensors of FIGS. 7 and 8.

FIG. 9 depicts an exploded view of the electrode shown in FIGS. 7 and 8. As shown, to enhance sensitivity of sensor 92 or 94 in some embodiments, a thin film 234 of electrolytic material, which may be the same material as the ionomer membranes of FIGS. 7 and 8, may optionally be placed on electrode 103 or 138 to increase the area of contact between the ionomer membrane 105 or 134, electrode 103 or 138, and gas to include the surface of electrode 103 or 138. Gas diffuses throughout film 234, which is in contact with the surface of electrode 103 or 138. As a result of the increased contact area, the sensing area is increased and response time is minimized. Gas diffuses faster through film 234 when film 234 has a minimal thickness. Hence, the thinner film 234 is, the faster the response time is for sensor 92 or 94.

Without film 234, the interface in the approximate area of electrode 103 or 138 would be substantially smaller, limited to an area where ionomer membrane 105 or 134 comes in contact with electrode 103 or 138. This contact area would generally be a linear contact point defining an approximate circumference of electrode 103 or 138.

In some embodiments, film 234 has a thickness less than 2 micrometers. Ideally, film 234 should be as thin as possible to maximize sensor response time and sensitivity. Hence, sensor 92 or 94 may further comprise film 234 having a thickness of less than 1 micrometer. A film having such reduced thickness permits faster gas diffusion and, thus, faster response times. Film 234 is an electrolytic medium, which includes all the limitations of ionomer membrane 105 or 134 and may be, but need not be, the same material as ionomer membrane 105 or 134.

Film 234 is in a solid state because it has more structural integrity than liquid state electrolyte, thereby permitting a consistently uniform thickness over electrode 103 or 138. This enhances sensor repeatability and facilitates functionality for liquid state electrolyte would be difficult to maintain in a fixed position on the surface of electrode 103 or 138.

Optionally, the response time of sensor 92 or 94 may further be improved by reducing the size of the inlet and outlet of each sensor 92 or 94. In this effort, the gas is more concentrated while inside the sensor due to there being less internal volume for the gas to disperse. Less dispersion and a more concentrated gas generally results in a more easily detected gas and, therefore, reduced response time of sensor 92 or 94. Hence, the volume in which gas may disperse is reduced. Such dispersion is generally referred to as axial dispersion because the dispersion is approximately along the axis containing a center point of sensor 92 or 94. In some embodiments, the inlet and outlet have a diameter of approximately 1 mm. The inlet and outlet need not be round but may be of any shape so long as gas may be injected into and extracted from sensor 92 or 94. Such shapes include 3 sided, 4 sided, or polygonal geometries.

Optionally, as shown in FIGS. 8 and 9, sensor 94 may also include cover 150 on ionomer membrane 134 for minimizing the vaporization or evaporation of electrolyte solution 152 as solution 152 is absorbed and passed upwardly through ionomer membrane 134. Cover 150 is in contact with the surface of ionomer membrane 134 opposite from substrate 132. Cover 150 does not block any portion of either diffusion hole 144 or electrode 138 because doing so would hinder gas detection and negatively affect sensor sensitivity. Cover 150 is not needed for sensor 66 to operate properly and may be eliminated in its entirety. For embodiments where sensor 94 includes cover 150, it is understood that the length L' of the diffusion path is the height of both ionomer membrane 134 and cover 150. For embodiments where sensor 94 does not include cover 150, length L' is the height of membrane 134.

Figure 10:
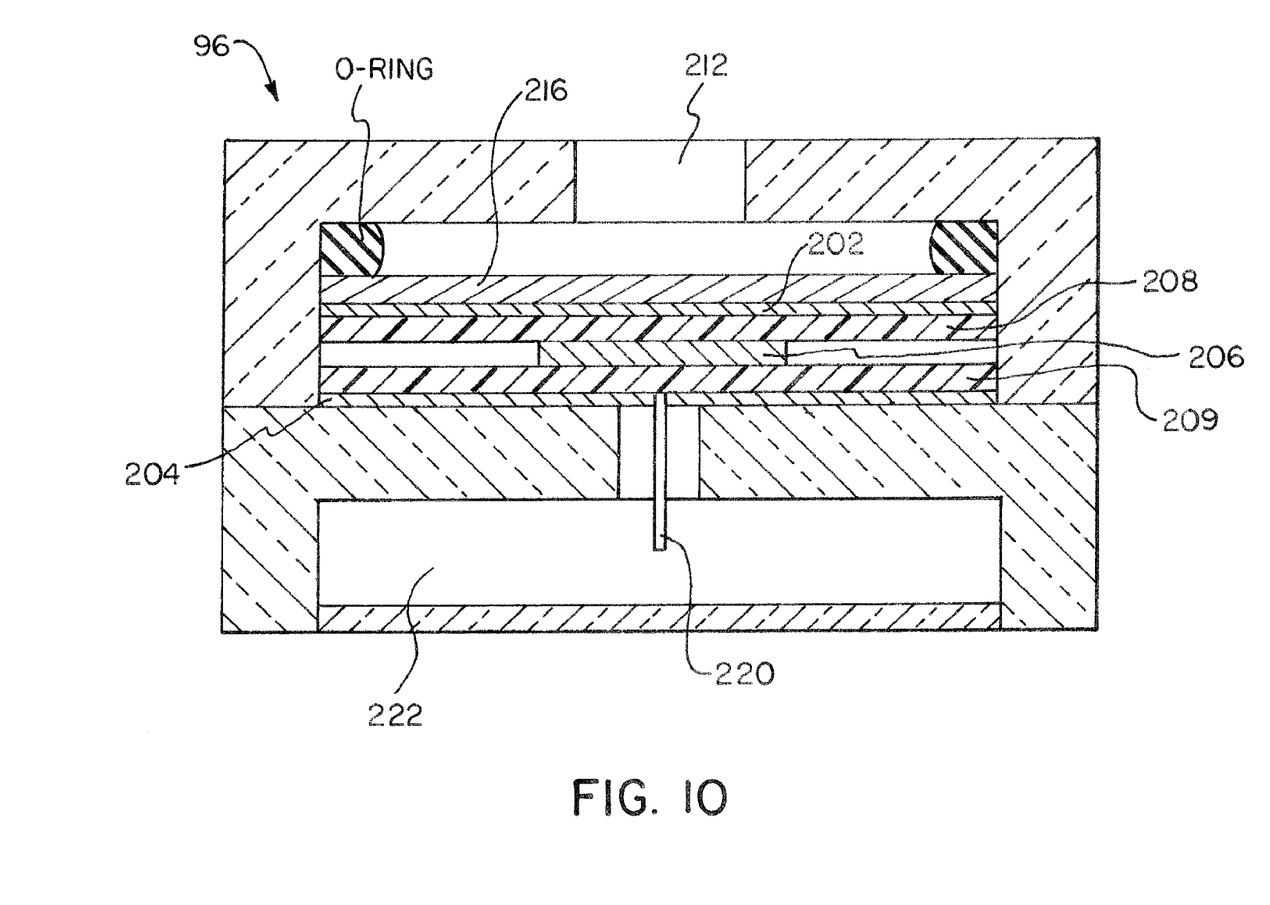
FIG. 10 depicts another sensor for use with the apparatus shown in FIG. 2.

FIG. 10 depicts another electrochemical gas sensor 96, which may, but not necessarily, be used as sensor 66. As shown, sensor 96 includes sensing electrode 202, counter electrode 204, and reference electrode 206.

Optionally sensor 96 includes filter 209 between counter electrode 204 and reference electrode 206 for wetting these electrodes. Further, filter 208 may be placed between sensing electrode 202 and reference electrode 206 for wetting these electrodes. Filter 208 includes the same limitations as filter 209.

Sensor 96 further includes gas inlet 212 for permitting gas to enter sensor 96 for detection upon reaction with ionomer membrane 216 and sensing electrode 202.

To draw electrolyte up from reservoir 222, wick 220 is in contact with the electrolyte solution in reservoir 222 and filter 208, which in turn is in contact with reference electrode 206, another filter 208, and sensing electrode 202.

Optionally, platinum contact strips may be placed in select areas of sensor 96 to enhance sensitivity and conductivity. A platinum strip may be placed between membrane 216 and sensing electrode 202, between reference electrode 206 and filter 208, between filter 209 and counter electrode 204, or all of the above.

Figure 11:
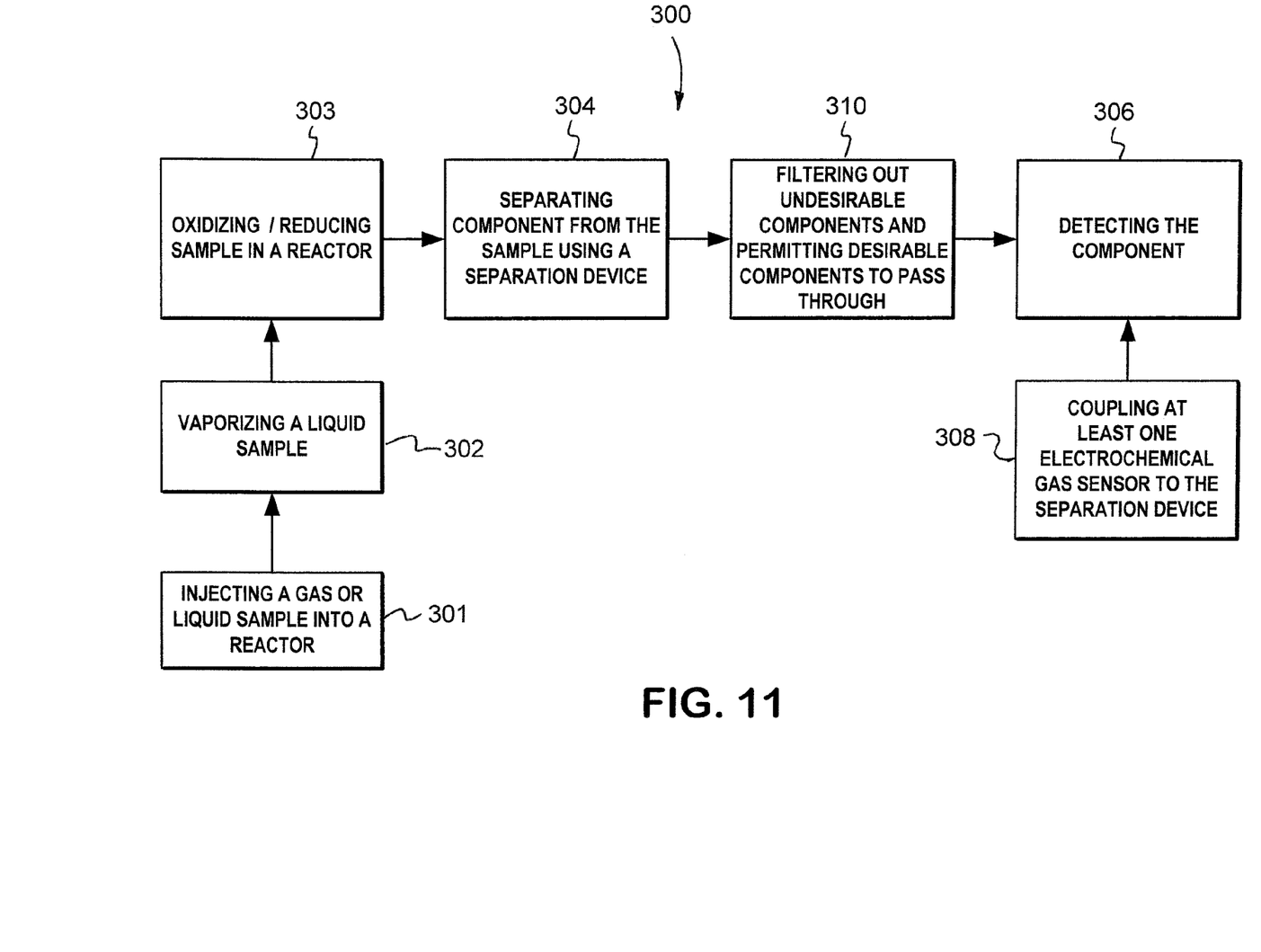
FIG. 11 depicts a method for providing the apparatus shown in FIG. 2.

FIG. 11 depicts a method 300 for determining a total concentration of a component in a gas sample. Method 300 includes injecting 301 the sample into a reactor, oxidizing or reducing 303 the sample in a reactor and separating 304 the desirable gas component to be detected from the gas sample using a separation device, which may be, a GC or other device for separating the desirable component(s) from the remainder of the gas sample. Method 300 also includes detecting 306 the desirable component(s) using a detection device, such as known or novel detectors and/or sensors.

If the sample is of a quantity that may be difficult to convert to a gaseous state, such as a sample greater than 1 ml, method 300 may optionally include the step of vaporizing 302 the sample (in a vaporizer) until it is converted to a gaseous state. For smaller quantities of liquid, the vaporizer may be omitted because the reactor, used for oxidizing or reducing 303 the sample, may also suffice in converting the sample in a liquid state to a gaseous state.

In further embodiments, method 300 may also include the step of coupling 308 at least one electrochemical gas sensor to the separation device for detecting 306 the component. In some of these further embodiments, method 300 may also include the step of providing a substrate having a surface, depositing an electrode on the surface, contacting an ionomer membrane with the electrode, providing an opening in the ionomer membrane in an approximate area of the electrode, introducing a gas into the opening toward the electrode, and simultaneously contacting the gas with both the electrode and ionomer membrane.

Moreover, method 300 may also include the step of filtering 310 out undesirable components and permitting desirable components to pass through to the detection step.

Although the invention has been described with reference to a particular arrangements of parts, features and the like, these are not intended to exhaust all possible arrangements or features, and indeed many other modifications and variations will be ascertainable to those of skill in the art.

What is claimed is:

1. An apparatus for determining a total concentration of a component in a sample, comprising:
   a reactor for oxidizing or reducing the sample;
   a chromatographic column coupled to said reactor for separating the component in the sample;
   an electrochemical gas sensor directly coupled to said chromatographic column for detecting the component;
   wherein said electrochemical gas sensor has a substrate, the substrate having a surface for depositing electrodes thereon,
   an ionomer membrane in contact with said substrate surface,
   the ionomer membrane having a first surface and a second surface,
   an electrode in contact with said substrate surface,
   an opening extending from said first surface to said second surface in a location proximate to said electrode for defining a passage; and
   a three way contact between said gas, electrode, and ionomer membrane within said opening wherein gas simultaneously contacts said electrode and said ionomer membrane.

2. A method for determining a total concentration of a component in a sample, comprising the steps of:
   oxidizing or reducing the sample in a reactor;
   separating the component from the sample using a separation device;
   directly coupling an electrochemical gas sensor to the separation device for detecting the component;
   providing a substrate having a surface for depositing electrodes thereon;
   depositing an electrode on the substrate surface;
   contacting an ionomer membrane with the electrode;
   providing an opening in the ionomer membrane in an approximate area of the electrode;

extending the opening from a first surface of the ionomer membrane to a second surface of the ionomer membrane for defining a passage; and placing a gas in the opening and contacting the gas simultaneously with the electrode and ionomer membrane within the opening.

3. The method according to claim 2, further comprising the step of separating the component from the sample using a gas chromatograph column.

4. The method according to claim 2, further comprising the step of coupling a plurality of electrochemical gas sensors to the separation device for detecting multiple components.

5. The method according to claim 2, further comprising the steps of filtering out undesirable components and permitting desirable components to pass through.

* * * * *